(12) United States Patent
Fichera

(10) Patent No.: US 7,553,451 B2
(45) Date of Patent: Jun. 30, 2009

(54) PLATFORM APPARATUS WITH HORIZONTAL SLIDE TRANSLATION AND METHOD

(75) Inventor: Stephen L. Fichera, Salem, NH (US)

(73) Assignee: Cytyc Corporation, Marlborough, MA (US)

( * ) Notice: Subject to any disclaimer, the term of this patent is extended or adjusted under 35 U.S.C. 154(b) by 911 days.

(21) Appl. No.: 10/954,796

(22) Filed: Sep. 29, 2004

(65) Prior Publication Data

US 2006/0073073 A1 Apr. 6, 2006

(51) Int. Cl.
*G01N 35/00* (2006.01)
(52) U.S. Cl. .............................. 422/63; 422/99; 422/104
(58) Field of Classification Search .................. 422/63, 422/65, 64; 359/393, 396; 435/287.3
See application file for complete search history.

(56) References Cited

U.S. PATENT DOCUMENTS

| | | | | |
|---|---|---|---|---|
| 4,424,191 A | * | 1/1984 | Jakubowicz | 422/65 |
| 4,584,275 A | * | 4/1986 | Okano et al. | 435/287.3 |
| 4,807,984 A | * | 2/1989 | Kurimura et al. | 359/393 |
| 6,020,995 A | * | 2/2000 | Dreyer et al. | 359/396 |
| 6,180,061 B1 | * | 1/2001 | Bogen et al. | 422/64 |
| 2002/0054830 A1 | * | 5/2002 | Bogen et al. | 422/64 |

* cited by examiner

*Primary Examiner*—Walter D Griffin
*Assistant Examiner*—Christine T Mui
(74) *Attorney, Agent, or Firm*—Vista IP Law Group LLP

(57) ABSTRACT

An apparatus and method for maintaining a slide in a substantially horizontal orientation while moving the slide between different elevations. A dual-hinge arrangement is utilized to maintain the slide in a horizontal orientation. A distal end of a second linking member is rotatably or pivotably coupled to a proximal end of a support member or finger. A distal end of the first linking member is also rotatably or pivotably coupled to the support member at a location between the distal and proximal ends of the support member. The proximal ends of the first and second linking members are connected to the base. The linking members are rotated, thereby resulting in movement of the slide between different elevations and remaining substantially horizontal as a result of the dual-hinge configuration. Linking members can also be coupled to a carrier member, the support members being coupled to the carrier. Thus, as the carrier member is raised and lowered by movement of the linking members, the support member and a slide thereon are also raised and lowered, the slide remaining substantially horizontal at different elevations. Further, the support members can be extended and retracted to, for example, interface with processing equipment or stations.

31 Claims, 23 Drawing Sheets

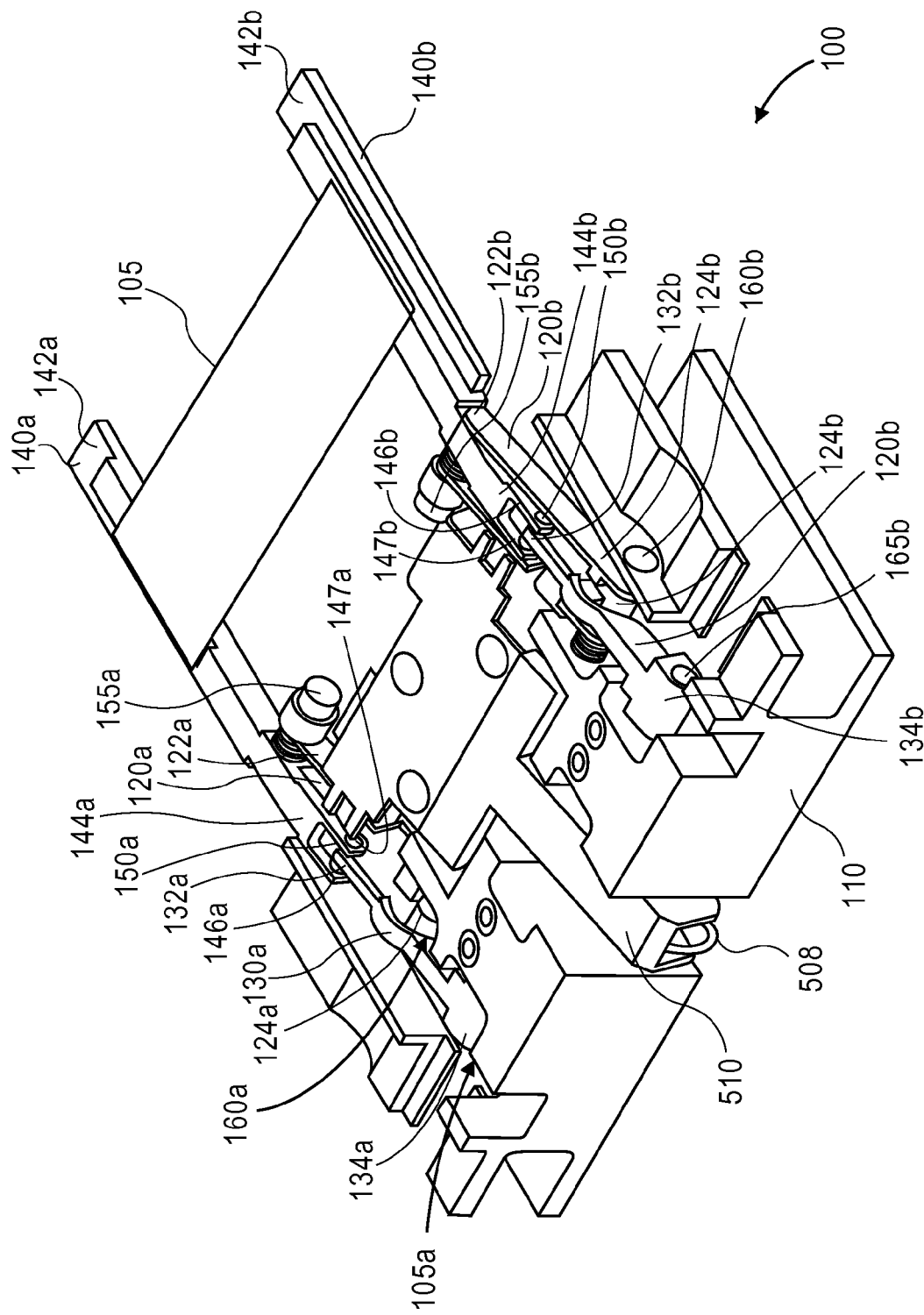

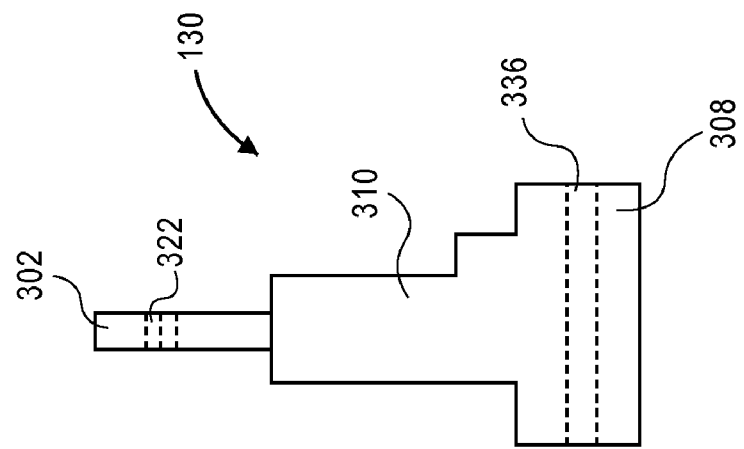
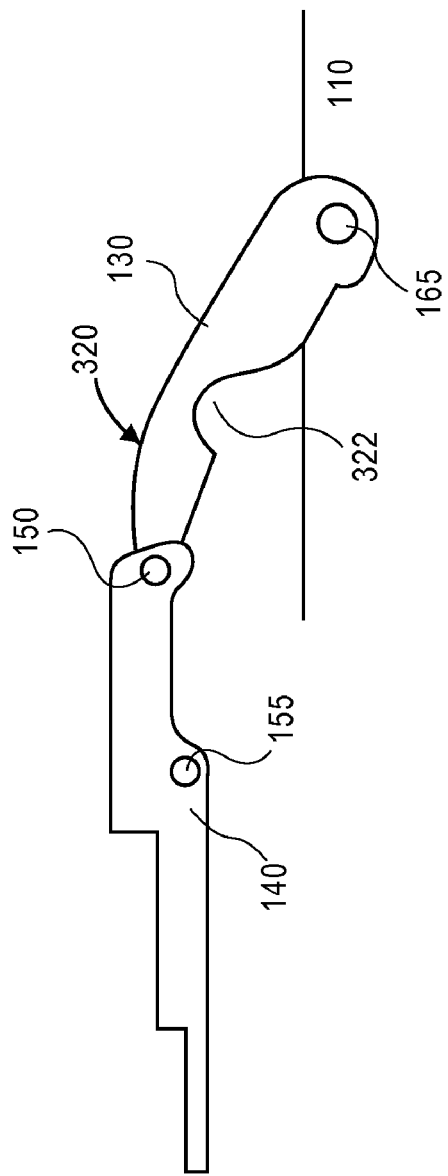
FIG. 3B
FIG. 3A

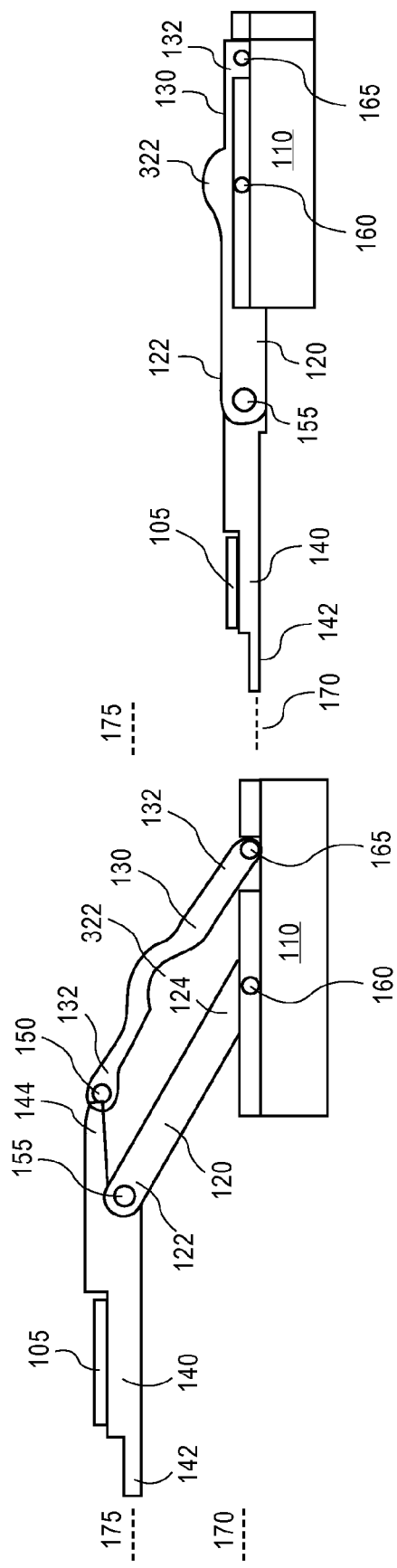

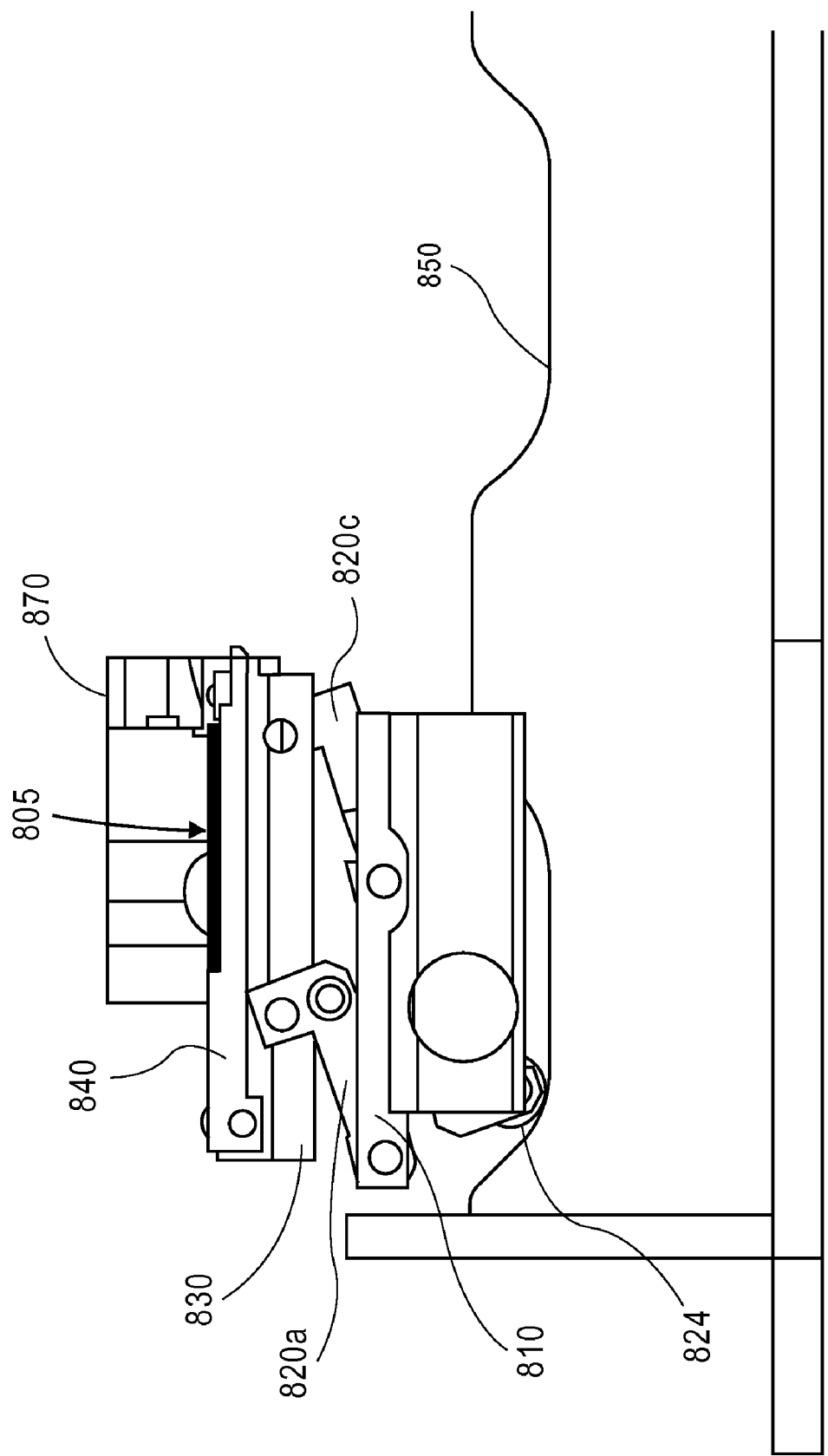

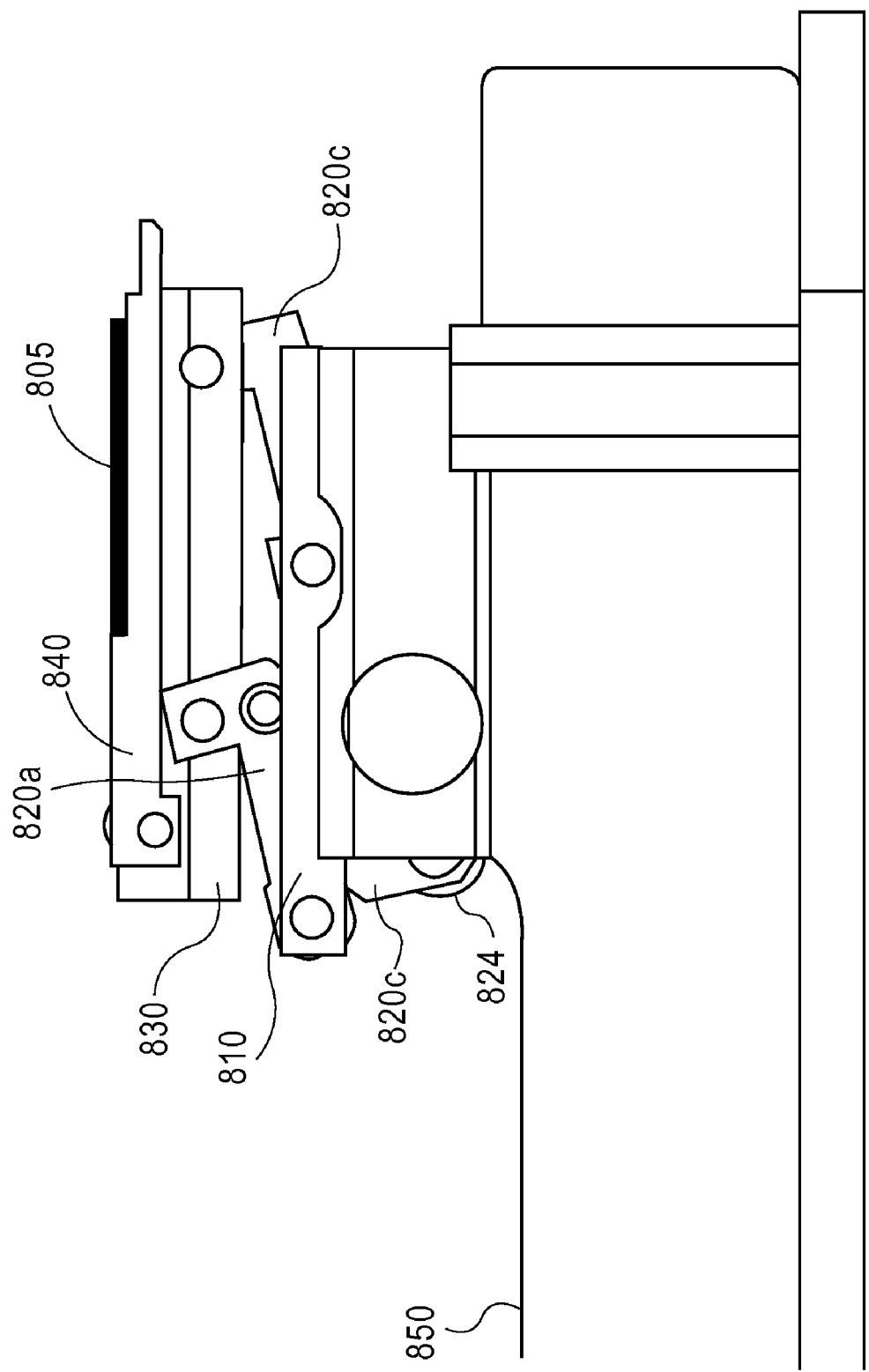

PLATFORM APPARATUS WITH HORIZONTAL SLIDE TRANSLATION AND METHOD

FIELD OF THE INVENTION

The present invention relates to platforms for carrying or transporting a slide, and, more particularly, to slide platforms that maintain a slide in a substantially horizontal orientation at different elevations.

DESCRIPTION OF RELATED ART

Medical professionals and technicians utilize glass or plastic test slides to conduct various cytological tests and analyses. New or unused slides are typically stored in a cartridge before a slide is prepared or processed, e.g., before a sample is applied to the slide. A slide selection or transport system typically picks or selects a slide from the cartridge and carries the slide to various processing or analysis stations. More specifically, the slide is typically supported or held by a support member, e.g., fingers, that extend from the platform. The platform and fingers attached thereto are advanced into the cartridge so that the cartridge releases a slide onto the fingers. The slide typically is not secured and simply rests freely on the fingers. As the system moves the platform and the slide thereon between stations, the platform is raised and lowered to adjust the position of the slide for a particular processing or analysis station.

More specifically, the system typically includes a cam that may initiate 10-15 rises and falls of the platform and the slide in order to deliver and position for the slide for a particular location or interface and then remove the slide when the processing is completed. During each rise and fall, the slide is pulled away and cantilevered up from a horizontal or flat position to an angled position as a result of the fingers rotating about a hinge. Consequently, each time a slide arrives at or departs from an interface, the fingers must be pushed down from the angled position to the horizontal position so that the slide can be provided to or withdrawn from an interface or processing or analysis station in a horizontal orientation.

Conventional slide platforms can be improved. For example, moving and positioning a slide between angled and horizontal orientations can be eliminated. As a result, it would no longer be necessary to push platform fingers down from an angled orientation to a horizontal position. Eliminating these adjustments also simplifies and improves mapping or positioning of the slide. Further, the wear and tear on the system can be reduced by eliminating the number of angular adjustments, thereby increasing the useful life of the system.

Additionally, eliminating the angular adjustments can also reduce offset loads on the slide, the support fingers, and the platform body, which are common with cantilevered systems. Further, a solenoid, a position sensor, and mapping software can be simplified or eliminated since it would no longer be necessary to include certain sensing components and mapping would be more accurate.

A need, therefore, exists for a slide platform that can move a slide between different elevations, while maintaining the slide in a substantially horizontal orientation without cantilever or angle adjustments.

SUMMARY

According to one embodiment, an apparatus for carrying a slide used in a specimen slide evaluation system includes a base, a support member and a plurality of linking members. The support member holds the slide. The linking members are coupled between the base and the plurality of support members. The support member remains substantially horizontal when the first and second linking members are actuated and the support member is translated between different elevations.

According to another embodiment, an apparatus for carrying a slide within a specimen slide evaluation system includes a base, a support member and a plurality of linking members. The support member includes a pair of fingers and the slide is placed across the fingers. Linking members are directly coupled between the base and the plurality of support members. The fingers remain substantially horizontal and in substantially the same lateral position when the first and second linking members are actuated and the fingers are translated between different elevations.

In accordance with another embodiment, an apparatus for carrying a slide within a specimen slide evaluation system includes a base, a support member for holding the slide, a plurality of linking members and a carrier. Linking members are coupled between the carrier and the base. The support member is coupled to the carrier so that the plurality of linking members are indirectly coupled between the base and the support member. The support member remains substantially horizontal when the first and second linking members are actuated and the support member is translated between different elevations. The support member is also moveable between a retracted lateral position and an extended lateral position.

In various embodiments, the support member can be a pair of fingers. The support member can remain in substantially the same lateral position while being translated between different elevations or, alternatively, can be moveable between different lateral positions. The linking members can be directly coupled between the base and the support member. The linking members can also be indirectly coupled. For example, linking members can be coupled between a carrier and the base, and the support member is coupled to the carrier. The carrier and support member connected thereto remain substantially horizontal when the carrier is translated between different elevations. Linking members can be rotatably coupled to the carrier and have various shapes depending on the design of the apparatus. Linking members can move together in unison, move through about the same angle and be rotatable in the same plane.

BRIEF DESCRIPTION OF THE DRAWINGS

Referring now to the drawings in which like reference numbers represent corresponding parts throughout:

FIG. 1A is a perspective view of an assembly according to one embodiment;

FIG. 3A is a partial side view of an assembly showing a second linking member and related components;

FIG. 3B is a top view of a second linking member;

FIG. 4A is a side view of connected first and second linking members in elevated and lowered positions;

FIG. 4B is a top view of connected first and second linking members in elevated and lowered positions;

FIGS. 9A-I illustrate operation of an assembly according to an alternative embodiment that obtains a slide from a slide cartridge and is translated between different elevations;

DETAILED DESCRIPTION OF ILLUSTRATED EMBODIMENTS

Figure 1B:
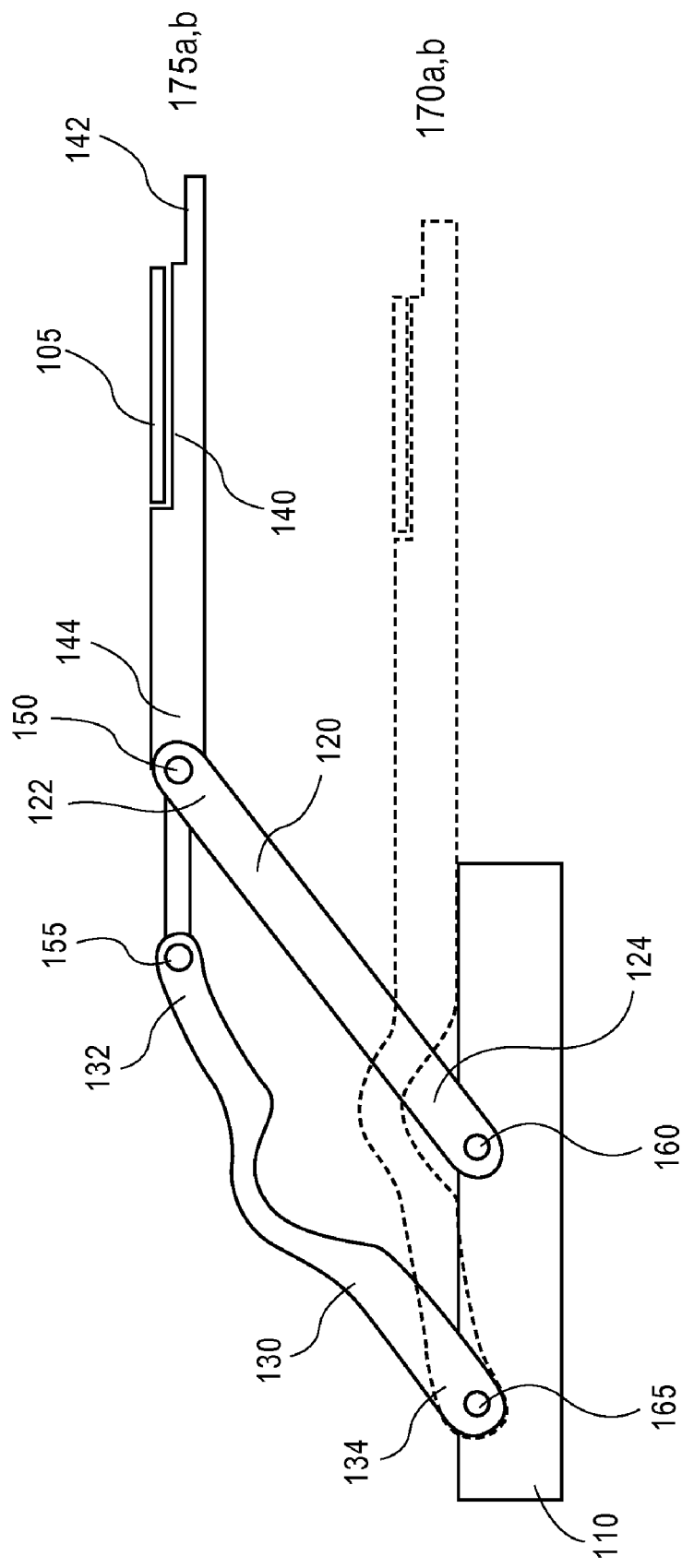
FIG. 1B is a partial side view of the assembly of FIG. 1A showing lowered and elevated support member positions.

In the following description, reference is made to the accompanying drawings which form a part hereof, and which show by way of illustration specific embodiments. It is to be understood that various changes to system components and configurations may be made.

FIG. 1A illustrates one embodiment of an apparatus 100 according to one embodiment. In the depicted embodiment, the apparatus 100 includes a base 110, first linking members 120a and 120b (generally 120), second linking members 130a and 130b (generally 130), and support members or fingers 140a and 140b (generally 140). The support members hold a slide 105 or other components used in slide preparation and processing having similar dimensions. For purposes of explanation and illustration, but not limitation, this specification refers to a slide 105.

The first linking members 120 have distal ends 122a and 122b (generally 122) and proximal ends 124a and 124b (generally 124). The second linking members 130 also have distal ends 132a and 132b (generally 132) and proximal ends 134a and 134b (generally 134). The fingers 140 have distal ends 142a and 142b (generally 142) and proximal ends 144a and 144b (generally 144). The proximal ends 144 of the fingers 140 include extensions or connection tabs 146a and 146b (generally 146) and 147a and 147b (generally 147).

Each finger 140 is attached to its respective first and second linking members 120 and 130 utilizing a dual hinge or dual linking member arrangement or other suitable dual-connector configurations. For example, in one embodiment, the distal ends 132 of the second linking members 130 are connected to the proximal ends 144 of the fingers 140 between the extensions 146 and 147 with hinges 150a and 150b (generally 150), and the distal ends 122 of the first linking members 120 are connected to the fingers 140 at a location between the distal and proximal ends 142 and 144 of the fingers 140 with hinges 155a and 155b (generally 155). Preferably, the location of the hinges 155 is closer to the proximal ends 144 of the fingers, but other dual hinge or dual linking member arrangements may be configured differently. Further, the hinges 150a and 150b and 155a and 155b are preferably positioned across from each other so that the fingers 140 move together between different elevations.

The proximal ends 124 and 134 of respective linking members 120 and 130 are coupled to the base 110, preferably to different locations on the base 110. For example, the proximal ends 124 of the first linking members 120 are rotatably or pivotably coupled to the base 110 with hinges 160a and 160b (generally 160), and the proximal ends 134 of the second linking members 130 are rotatably or pivotably coupled to a different point on the base 110 with hinges 165a and 165b (generally 165). If necessary, the hinges 165 may be adjustably secured (e.g., eccentrically or slidably coupled). For example, the position of the attitude of the fingers 140 may be adjusted without changing the arc rotation of the fingers. Thus, the fingers may be adjusted and oriented as needed so that they can interface with various processing and analysis stations.

Referring to FIG. 1B, the double hinge or double linking member configuration enable the fingers 140 to be moved or translated from a lower or first elevation 170 to a second or higher elevation 175 or from the elevated position 175 down to the lower position 170 while the fingers 140 and the slide 105 thereon remain in a substantially flat or horizontal orientation when moved between different elevations. Thus, rotating the linking members 120 and 130 about their respective hinges 160 and 165 results in raising and lowering horizontal fingers 140.

Having generally described an apparatus 100 according to one embodiment and the manner of its operation, this specification describes individual apparatus 100 components, how these components are assembled and operate together, and a method of translating a slide between different elevations while maintaining the slide in a substantially horizontal orientation. FIG. 1A illustrates an apparatus 100 having two sets (a,b) of similar components, one set on each side of the base 110. Different systems, however, may utilize different linking member, hinge, and support member configurations, e.g., one support member for holding a slide or two support members for holding a slide. For purposes of explanation and ease of understanding, this specification refers to these components and their corresponding general numeric identifiers rather than a particular set or component (a,b), unless a particular component is discussed.

Figure 2B:
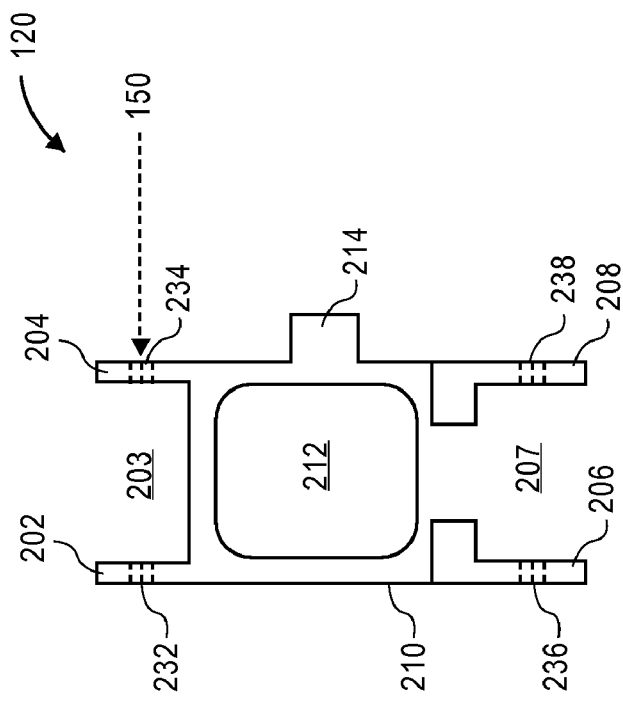
FIG. 2B is a partial top view of a first linking member.
Figure 2A:
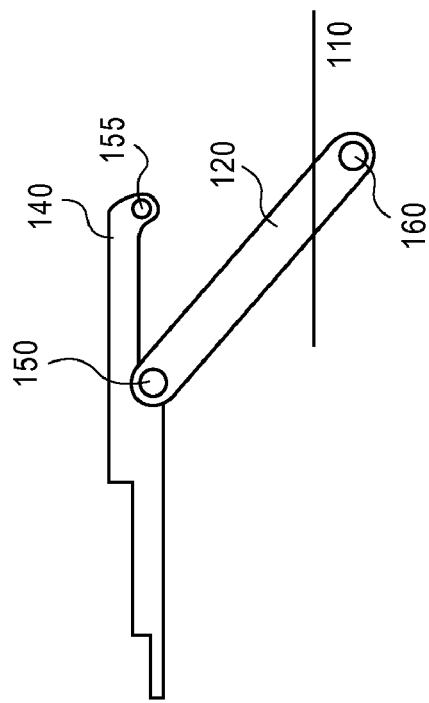
FIG. 2A is a partial side view of an assembly showing a first linking member and related components.

Turning now to FIGS. 2A-B, various first linking members 120 can be utilized with embodiments. In the depicted embodiment, the first linking member 120 is generally straight member with connectors at the ends thereof. The first linking member 120 is also shaped to coincide with or receive the second linking member 130.

More specifically, referring to FIG. 2B, the first linking member 120 includes a distal first arm or segment 202, a distal second arm or segment 204, a proximal first arm or segment 206, a proximal second arm or segment 208, and a middle section 210 between the distal and proximal arms. The distal and proximal arms define respective openings or spaces 203 and 207. A middle cavity 212 is formed within the middle section 210. A tab 214 extending from a side of the middle section 210 provides a contact point between the first linking member 120 and an engagement plate (not shown in FIGS. 2A-B).

The distal arms 202 and 204 define apertures 232 and 234 through which a rod or hinge 150 extends to attach the first linking element 120 and the finger 140 together. Similarly, the proximal arms 206 and 208 define apertures 236 and 238 through which a rod or hinge 160 extends to rotatably couple or attach the proximal ends 206 and 208 of the first linking element 120 to the base 110.

Referring to FIGS. 3A-B, the second linking member 130 includes a distal end 302, a proximal end 308, and a middle section 310 between the distal and proximal ends 302 and 308. In the depicted embodiment, the proximal end 308 is wider than the middle section 310, which is wider than the distal end 302. The second linking member 130 also has a slightly arcuate shape 320 with a receiving cavity 322.

The distal end 302 defines an aperture or cavity 332 through which the second hinge 150 extends to connect the finger 140 and second linking member 130 together. The proximal end 308 defines an aperture or cavity 336 through which the base hinge 165 extends to rotatably couple the second linking element 130 and the base 110 together.

Figure 4C:
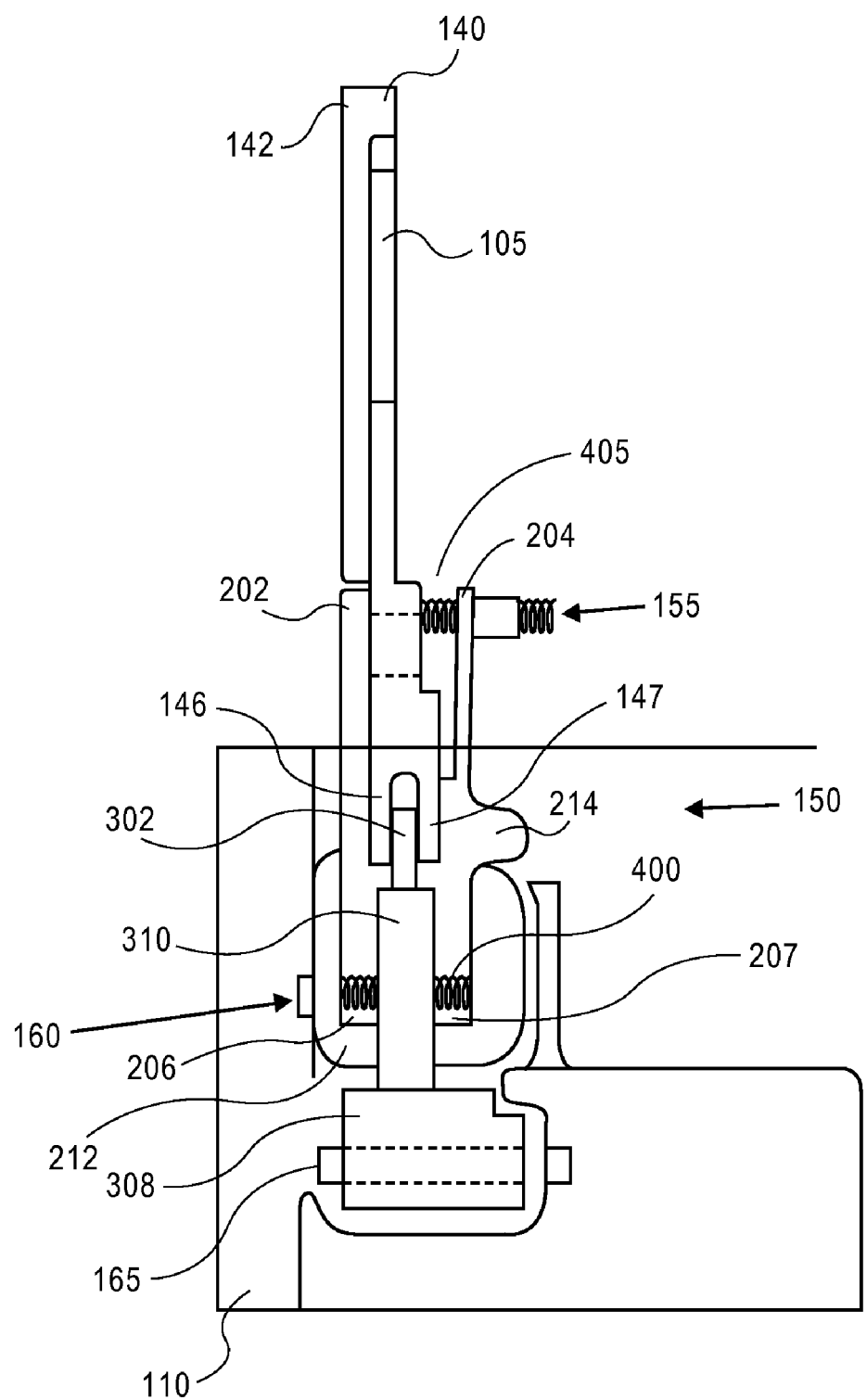
FIG. 4C is a top view of connected first and second linking members in a lowered position.
Figure 5:
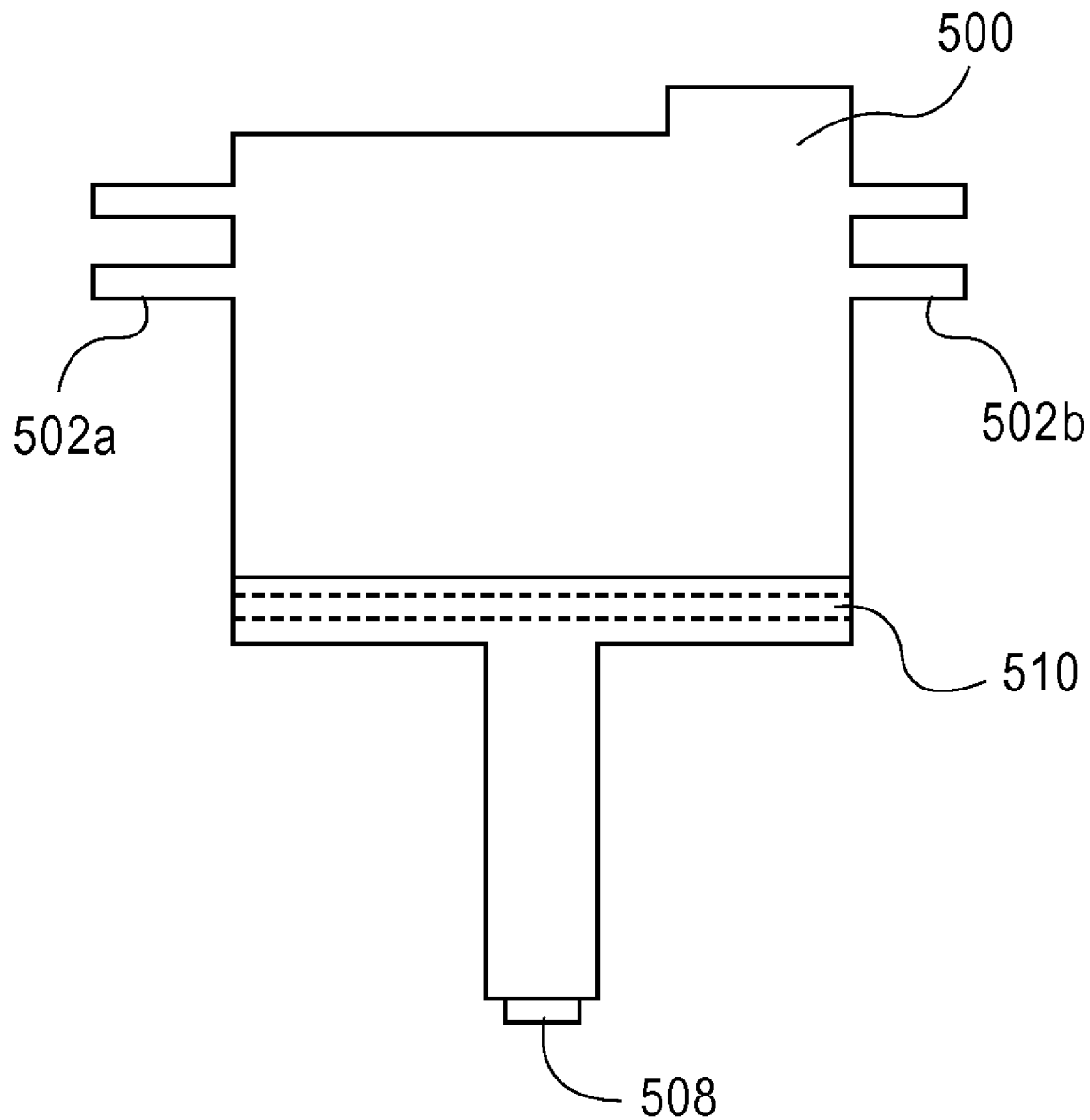
FIG. 5 is a partial top view of the assembly of FIG. 1.

Having described aspects of the first and second linking members 120 and 130 individually, FIGS. 4A-C illustrate other views of the apparatus 100 shown in FIGS. 1A-B in which the first and second linking members 120 and 130 are connected between a finger 140 and the base 110. More specifically, a distal end 132 of the second linking member 130 is coupled to a proximal end 144 of the finger or support member 140 between the extensions 146 and 147. A distal end 122 of the first linking member 120 is coupled to the finger or support member 140 at a location between the distal and proximal ends 142 and 144 of the finger 140, preferably at a location closer to the proximal end 144.

The proximal ends 124 and 134 of the first and second linking members 120 and 130 are rotatably coupled to different locations on the base 110 with hinges 160 and 165 or other suitable connectors. A spring 400 is provided with the hinge 160 to bias the first linking member 120 (and the finger 140 attached thereto) to the elevated position 175. A spring 405 is also provided around the hinge 155 to provide further support to the finger 140 in a generally horizontal orientation by biasing the distal ends 142 of the fingers 140 upwards in order to take up any tolerances or clearances.

With this configuration, the first and second linking members 120 and 130 rotate about separate hinges 160 and 165. The linking members 120 and 130, however, rotate in the same plane and in the same general direction since they are aligned with each other, and both of the linking members 120 and 130 are connected to a single finger 140.

In the elevated position 175, shown in FIG. 4A, a portion of the second linking member 130 is positioned above a portion of the first linking member 120. When the first and second linking members 120 and 130 are rotated down from the elevated position 175 to the lower position 170, shown in FIG. 4B, a portion of the second linking element 130 is received or placed within the first linking element 120. Specifically, as shown in FIG. 4B, the spring 400 and the hinge 160 are placed with the arcuate receiving cavity 322. Further, a proximal end 144 of the finger 140 is placed within the cavity 212 of the first linking member 120.

Referring to FIGS. 1, 5 and 6A-C, when the apparatus 100 is used as part of a slide transport system, the apparatus 100 is moved to and from various processing and analysis stations, such as a slide cartridge. In use, the spring 400 upwardly biases the first linking member 120 against an engagement plate 500, which is attached to a T-shaped pivot arm 510 that extends through a middle portion of the base 110. A roller 508 is rotatably coupled to flange of the pivot arm 510. In use, the roller 508 follows a cam 505, thereby moving the pivot arm 510 which, in turn, translates the fingers between initial and elevated positions.

Figure 6A:
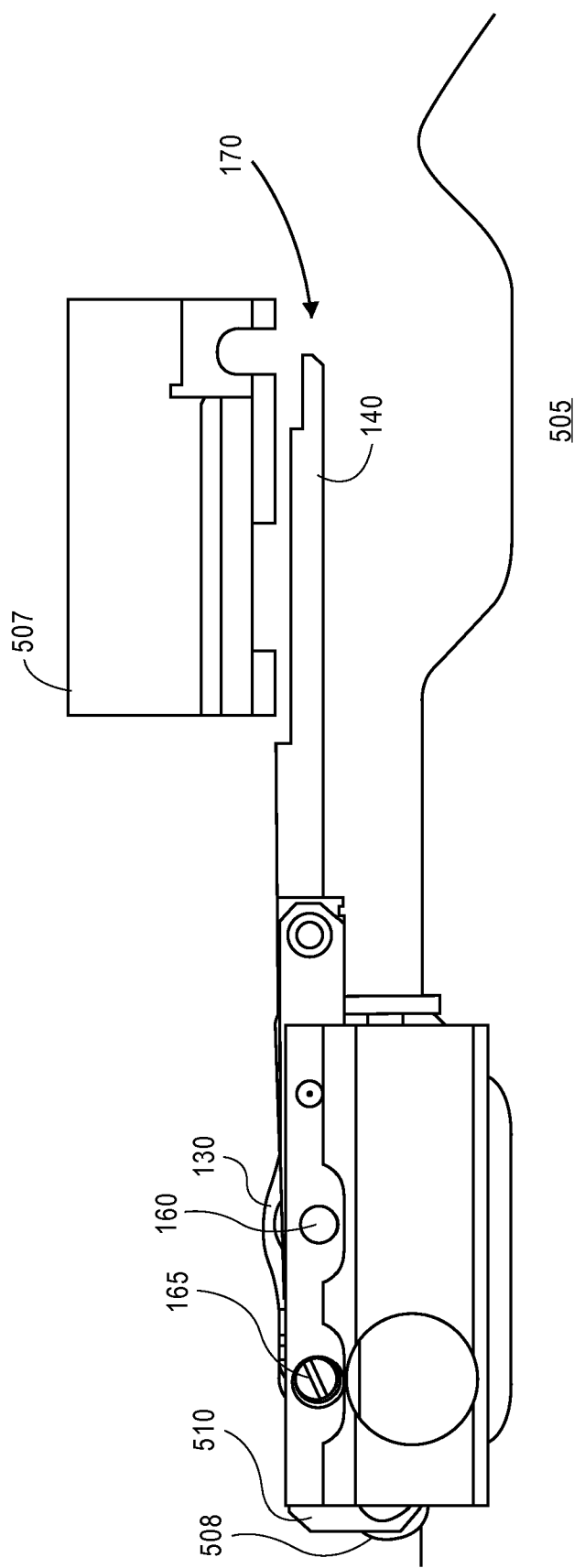
FIGS. 6A-C illustrate operation of an assembly according to one embodiment that obtains a slide from a slide cartridge and is translated between different elevations.
Figure 6B:
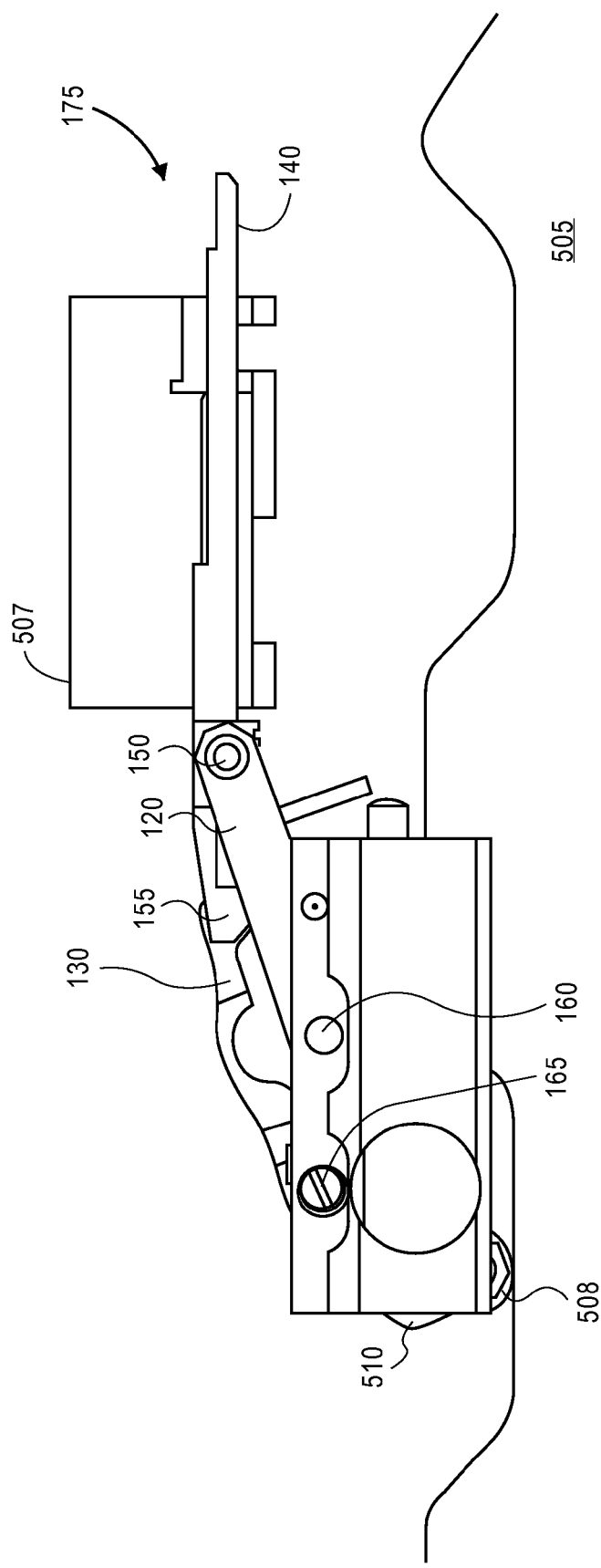
Figure 6C:
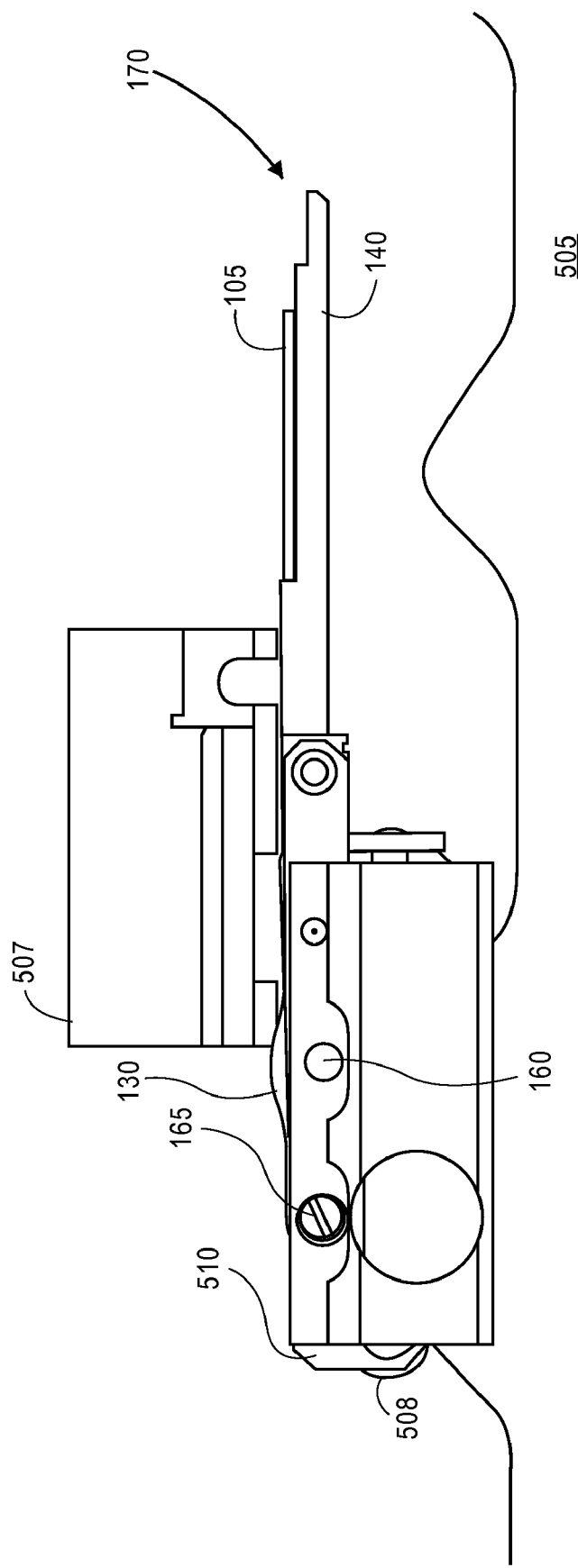

More specifically, as shown in FIGS. 6A-C, the apparatus 100 moves along the cam 505 to a slide cartridge 507 to pick a slide from the cartridge and transport the slide to the next station. During the selection and transportation of the slide, the pivot arm 510 and the engagement plate 500 attached thereto can rotate to different angles about a rod or hinge while remaining substantially horizontal.

For example, in the depicted embodiment, the first linking member 120 and the pivot arm 510 share a common hinge 160. The hinge 160 extends through an aperture in a flange of the pivot arm 510, a section of the base 110, and the distal ends 124 of the first linking member 120. Various known fasteners can be used to secure the ends of the rod or hinge 160 to the base 110. With this arrangement, the spring 400 that is placed around the hinge 160 biases the first linking member 120 against a bottom surface of the engagement plate 500, such as the bottoms of lateral extensions 502a and 502b (generally 502).

Initially, as shown in FIG. 6A, the pivot arm 510 and the engagement plate 500 are maintained in an initial horizontal or non-angled position as the apparatus moves along the cam 505 and initially approaches the cartridge 507. Referring to FIG. 5C, as the apparatus moves further along the cam and to the cartridge 507, the engagement plate 500 or the pivot arm 510 is released by the roller 508 following the cam 505 and the pivot arm 510 and the engagement plate 500 rotating upward at an angle. The spring 400 pushes up against the bottom of the first linking member 120 so that the tab 214 of the first linking member 120 pushes up against the extensions 502. The first linking member 120 rotates when the pivot arm 510 and the engagement plate 500 rotate, and the second linking member 130 also rotates upward since the first and second linking members 120 and 130 are connected through the fingers 140. A slide is then picked from the cartridge and placed on the fingers, as shown in FIG. 8D. Thus, the fingers 140 shift or translate from an initial substantially horizontal position 170 to an elevated substantially horizontal position 175. If necessary, the tab 214 may include adjustment components that can be used to adjust individual heights and attitude of the fingers 140a to properly interface with the cartridge and slides.

In addition to interfacing with a slide cartridge, the translation system according to embodiments can also transport the apparatus 100 to other analysis or processing stations, such as a printer for printing a label on a slide. The translation system can then move the apparatus 100 to a scanner for reading information stored on the label or to an analysis or processing station or interface. Mapping software is utilized to determine the location of the slide 105 on the support fingers 140 during these shifts and movements. Indeed, persons of ordinary skill in the art will recognize that embodiments can be used with various translation processing and analysis systems. Thus, a specific translation system is not discussed in further detail.

Figure 7:
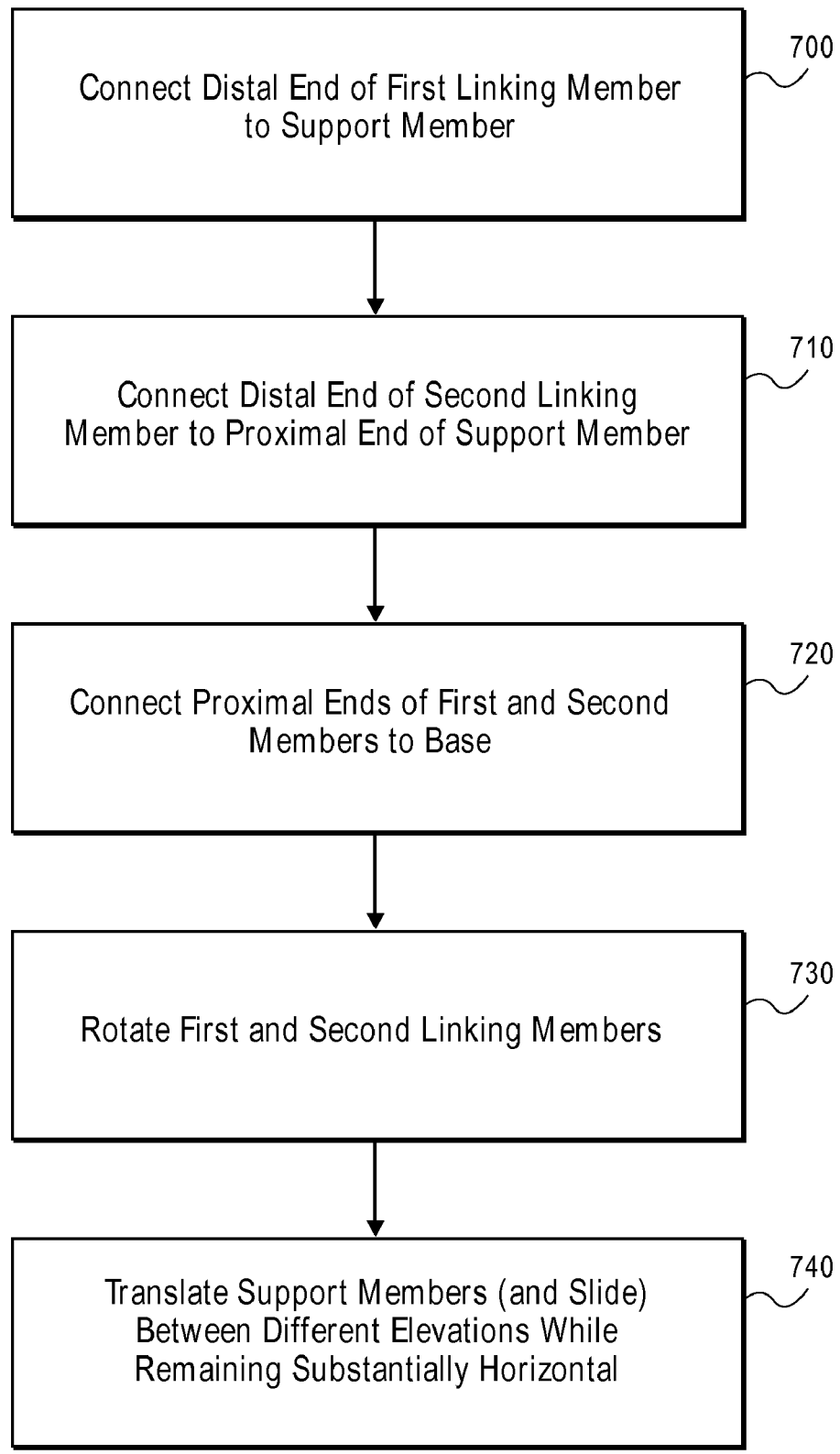
FIG. 7 is a system flow diagram illustrating how a slide is maintained in a substantially horizontal orientation at different support member elevations according to one embodiment.

FIG. 7 illustrates a method of moving a slide between a first position and a second, elevated position while retaining the slides in a substantially horizontal orientation. Initially, in step 700, a distal end of a first linking member is connected to the support member or finger. In step 710, a distal end of a second linking member is connected to a proximal end of a support member or finger. In step 720, the proximal ends of the first and second linking members are connected to the base, preferably, rotatably connected to different locations of the base. In step 730, the first and second linking members are rotated, e.g., by an engagement plate that is actuated by a cam or other actuation device. As a result, in step 740, the fingers and the slide thereon are translated or shifted between an initial elevation and a second elevation while the slide remains substantially horizontal.

Figure 8:
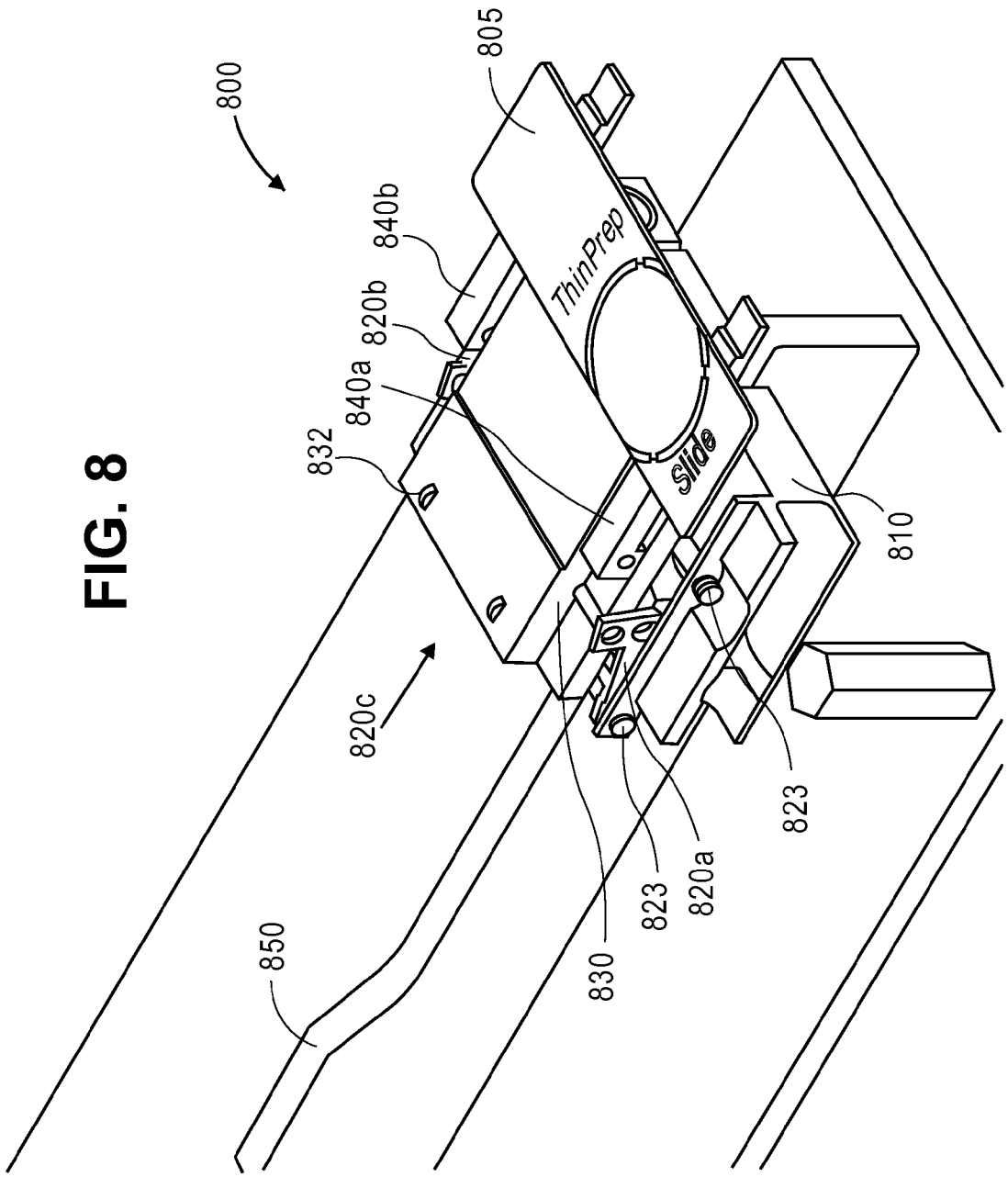
FIG. 8 is a perspective view of an alternative embodiment of an assembly.

An alternative embodiment of an apparatus 800 is shown in FIG. 8 and its operation is shown in FIGS. 9A-I. This alternative embodiment utilizes the same or similar components as the embodiment shown in FIG. 1 and operates in a similar manner. The apparatus 800 shown in FIG. 8, however, includes linking members that are attached to a carrier member 830, which is translated between different elevations. A support member 840, such as support fingers, are coupled to the carrier member. Thus, linking members are indirectly attached to a support member 840, which are elevated and lowered by raising and lowering the carrier member 830.

Further, in the apparatus 800, the fingers 840 can be retracted in an out of the carrier 830, or extend outwardly from the carrier if the fingers do not rest inside the carrier, while at different elevations. Thus, the fingers 840 and the slide 805 carried by the fingers 840 are maintained in a substantially flat or horizontal orientation when moved between different elevations, and can be extended and retracted as necessary.

More particularly, the apparatus 800 includes a base 810 and a plurality of linking members. In the illustrated embodiment, three linking members 820a-c (generally 820) are utilized. Persons skilled in the art will appreciate that other numbers of linking members can be used with different apparatus configurations.

The ends of the linking members 820 define apertures through which a rod or hinge or other connector 823 extends for rotatable or pivotal attachment to the base 810 and/or carrier 830. Linking members 820a and 820b are located on opposite sides of the base 810. Proximal ends of linking members 820a and 820b are coupled to the base 810 and distal ends of the linking members 820a and 820b are coupled to the carrier 830. The linking members 820a and 820b can be "L" shaped with connection points at the ends thereof or other suitable shapes, such as straight members.

A third linking member 820c (shown in FIGS. 9B-D), extends between the carrier 830 and the base 810, in the middle of the base 810. A distal end of the linking member 820c (see FIGS. 9B-D) is connected to the carrier 830. A proximal end of the linking member 820c includes a roller 824 and follows the cam 850. Thus, in the alternative embodiment shown in FIG. 8, the linking members 820 are not coupled directly to the support member or fingers 840. Rather, the linking members 820 are coupled directly between the base 810 and the carrier 830, which is directly connected to the support member 840. In other words, the linking members 820 are indirectly coupled between the base 810 and the support member 840.

Support members or fingers 840 are coupled to the carrier 830. The fingers 840 can be inside or outside of the carrier 830 and be extended from or outside and retracted to or inside the carrier 830 (as generally shown by arrows in FIGS. 9H and 9I showing fingers 840 being extended from the carrier 830). In other words, the fingers 840 can assume different lateral positions (retracted and extended) relative to the carrier 830. Moving the support member 840 to different lateral positions may be helpful when interfacing with processing system components, such as a slide cartridge 870, a scanner or a printer, or transferring to, or straddling, other components/assemblies.

Persons skilled in the art will appreciate that various mechanisms can be used to retract and pull back the fingers 830 as the apparatus 800 traverses the cam 850. The following mechanisms are exemplary mechanisms that can be used.

Figure 10:
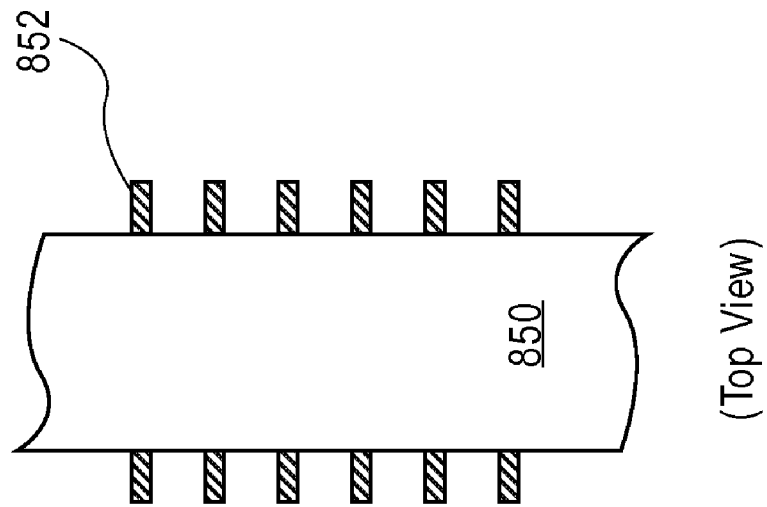
FIG. 10 illustrates one example of a mechanism that can be used to extend and retract a support member for a slide.
Figure 10:
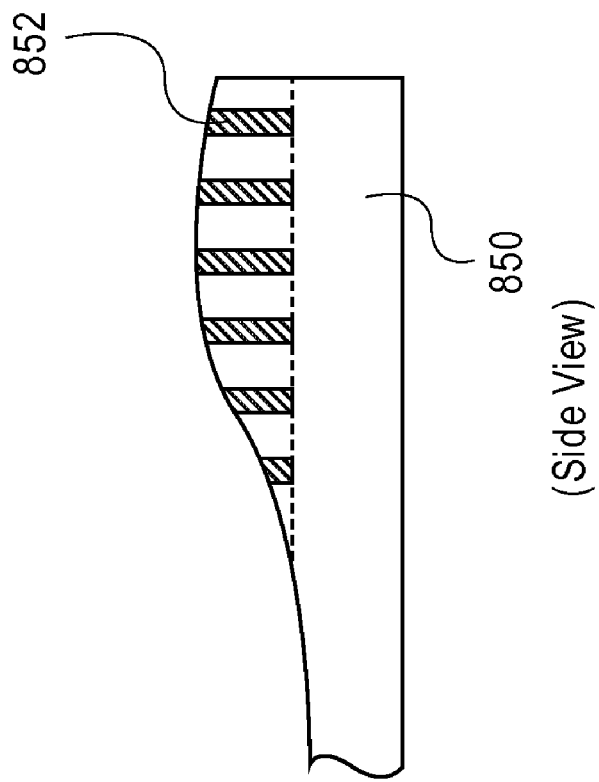
Figure 11:
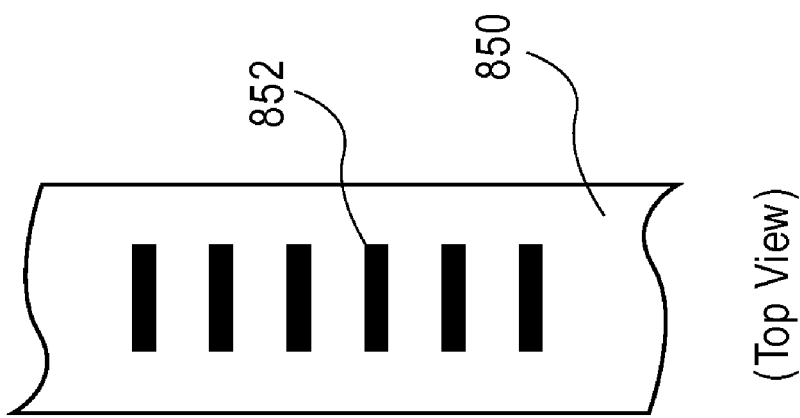
FIG. 11 illustrates a further example of a mechanism that can be used to extend and retract a support member for a slide.
Figure 11:
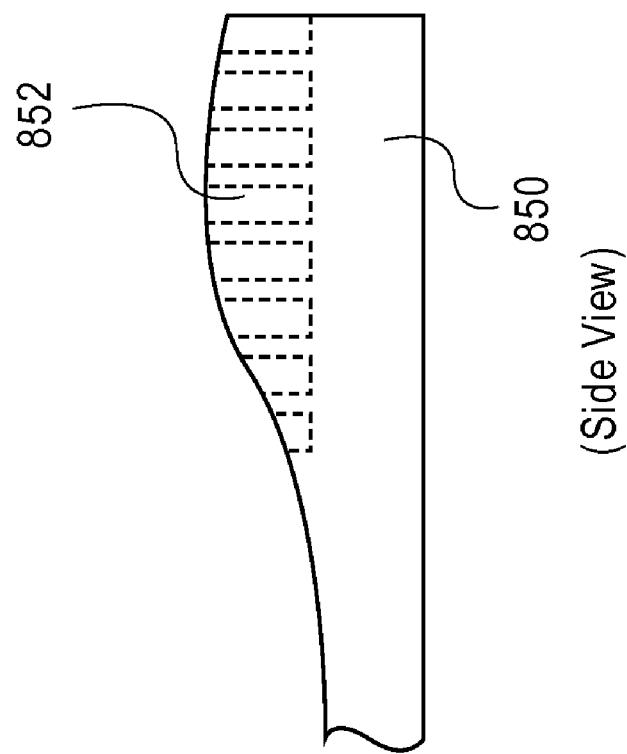

For example, one suitable retraction and extension mechanism may involve a pivot arm that extends down from the fingers or a gear assembly. As shown in FIGS. 10 and 11, a gear assembly may involve teeth 852 being formed in the exterior surface of the cam 850, as shown in FIG. 10, or on an interior surface of a cam 850, as shown in FIG. 11. A support member for the fingers 840 can include teeth corresponding to the teeth 832 formed in the cam 850. Thus, as the unit traverses the cam 850, the unit eventually traverses the cam teeth 852, thereby retracting or extending the fingers 840 from the carrier 830.

Another actuation arm can extend down from the carrier 830. When the actuation arm engages a tang or protrusion extending up from the cam 850, the actuation arm is rotated or displaced, thereby forcing the fingers 840 from a retracted position to an extended position or vice versa. For example, the actuation arm may displace a cross bar that extends across the width of the carrier 830, the fingers 840 being coupled to the cross bar. Displacing the cross bar also displaces the fingers 840. The fingers 840 can be placed back in to the retracted position if the apparatus reverses, thereby engaging the tang or protrusion, and rotating or displacing the actuation arm in an opposite direction, thereby retracting the fingers 840 to their home position.

Other systems may involve the use of a solenoid or magnetic components. For example, the cam or other section of a processing station can include a magnet that repels or attracts a member connected to the fingers 840, thereby pushing or pulling the fingers 840 to extend or retract the fingers 840. Persons skilled in the art will recognize that many other mechanisms can be used to extend and retract fingers 840, as necessary, and the devices discussed herein are exemplary mechanisms.

In use, the assembly 800 travels along the cam 850, as shown in FIGS. 9A-I. The roller 824 of the linking member 820c traverses different cam 850 levels, and the linking members 820 are actuated, resulting in the carrier 830 and the support member 840 coupled thereto being raised and lowered or translated between different elevations. Thus, the fingers 840 and the slide 805 (if a slide has been placed on the fingers) are maintained in a substantially horizontal orientation. The carrier 830 can include rollers 832, for reducing the friction between the apparatus 800 and slide processing stations as the apparatus 800 approaches and leaves processing stations along the cam 850. For example, as shown in FIGS. 9A-I, the apparatus 800 may traverse the cam 850 to pick a slide 805 from a slide cartridge 870 which is provided to a printer or other processing device or equipment.

Figure 9A:
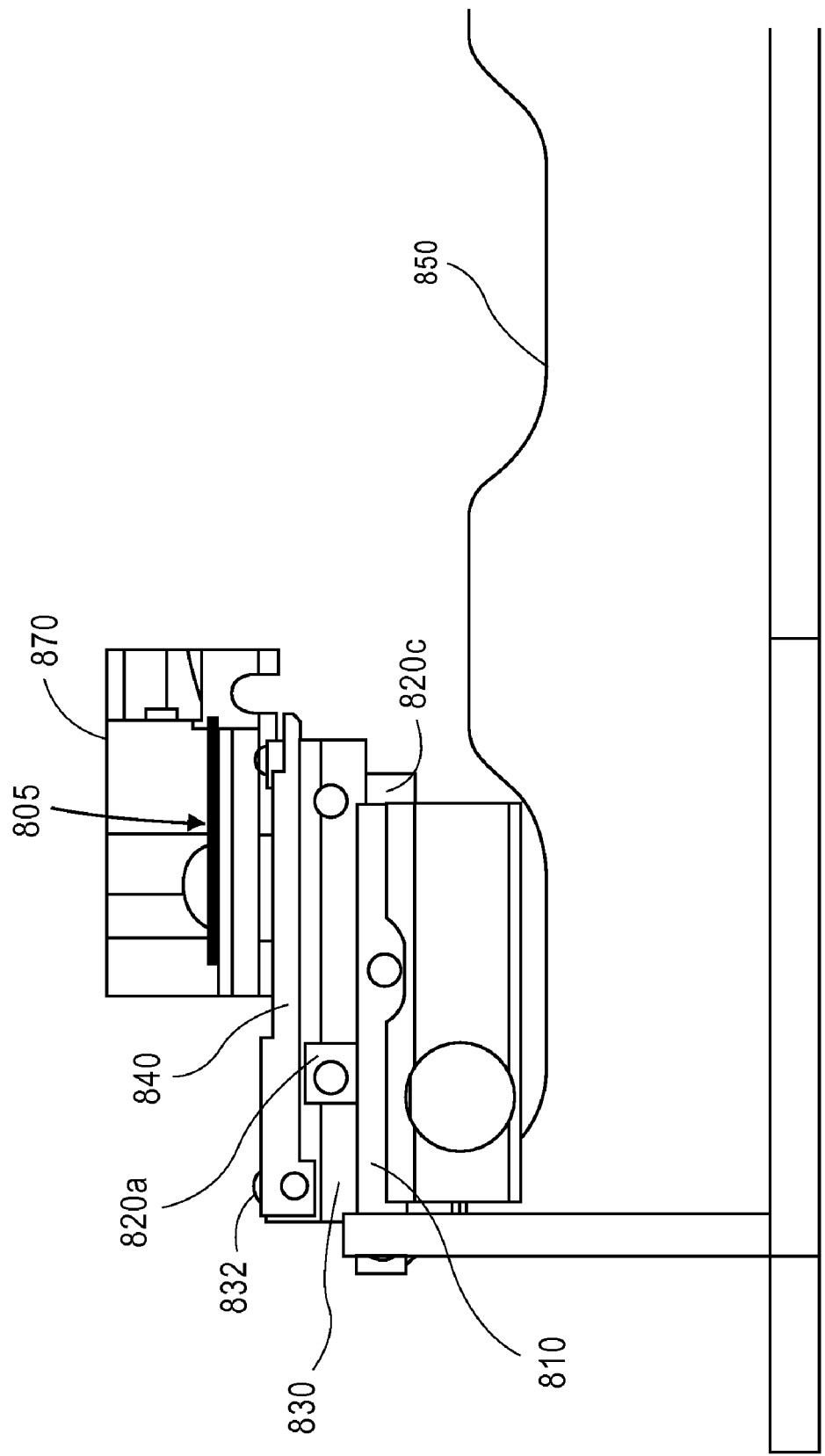
Figure 9B:
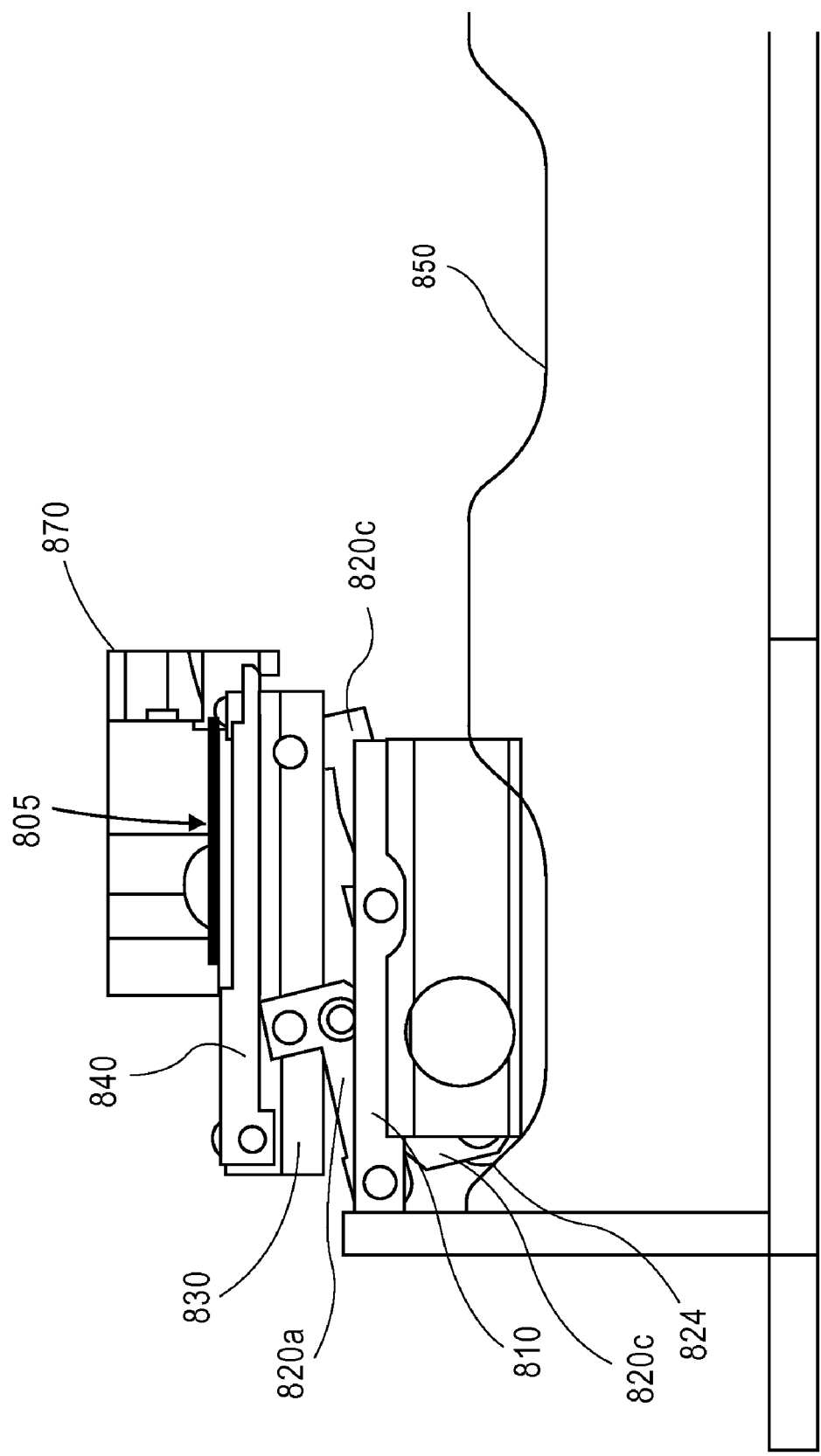
Figure 9D:
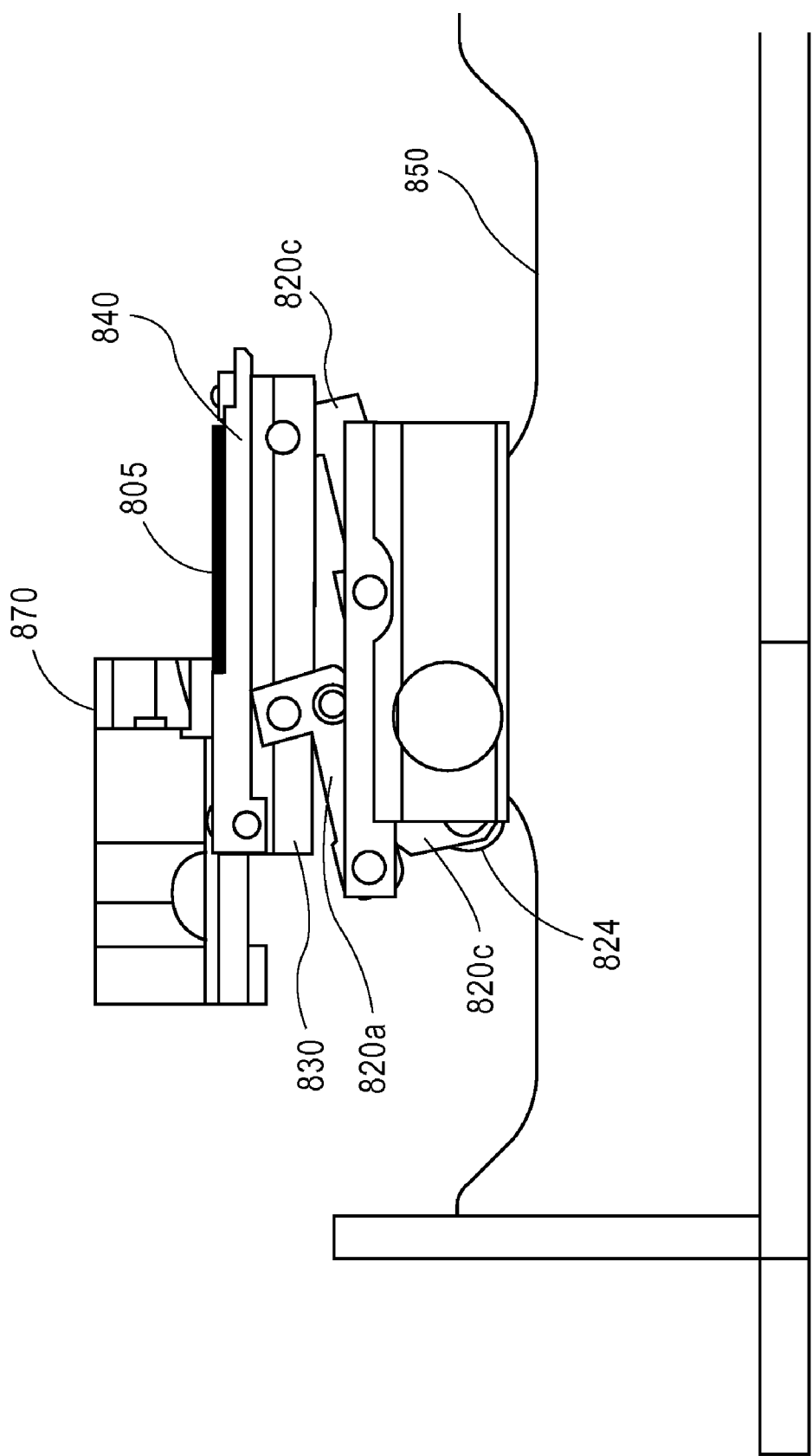
Figure 9E:
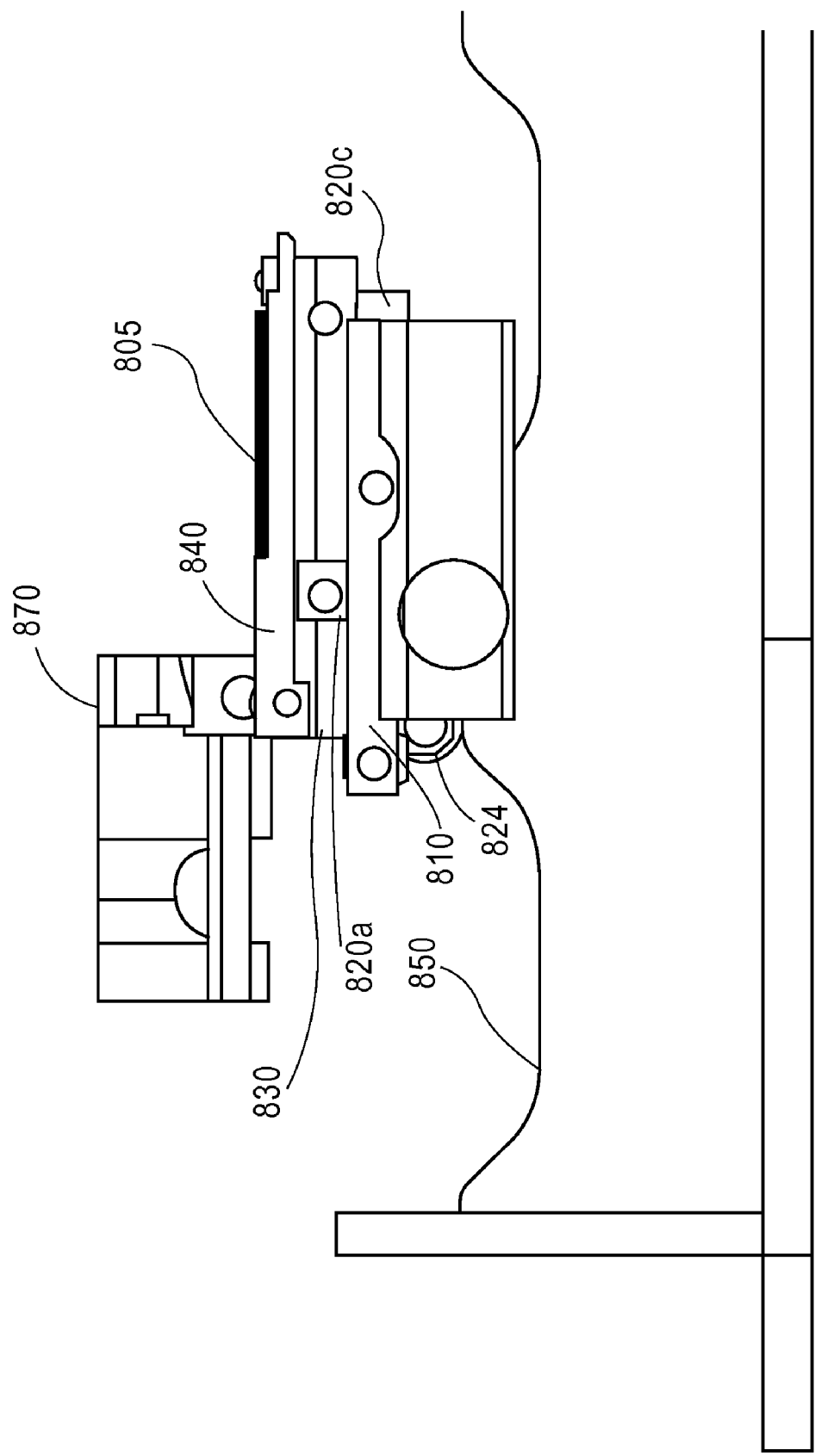
Figure 9G:
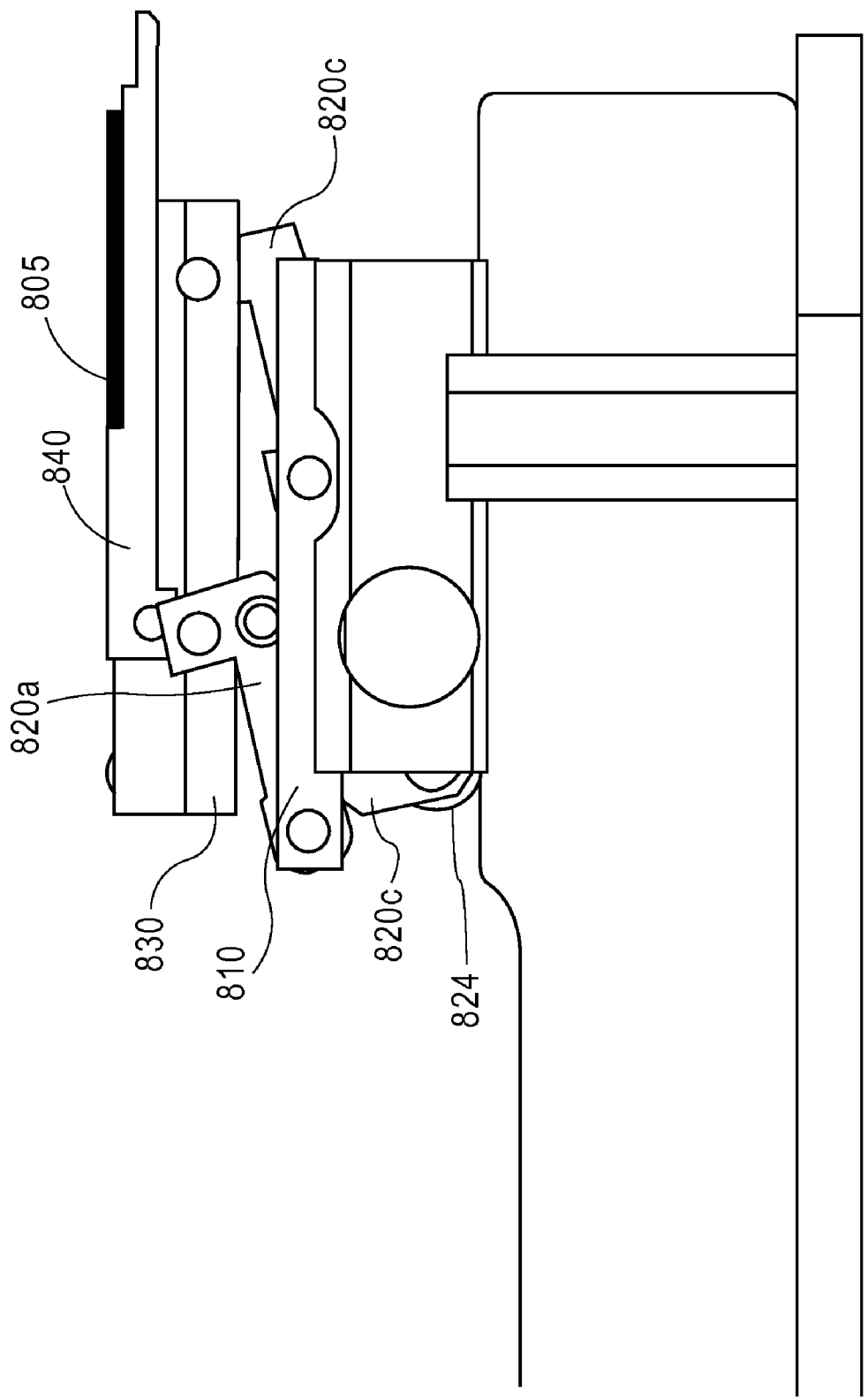
Figure 9H:
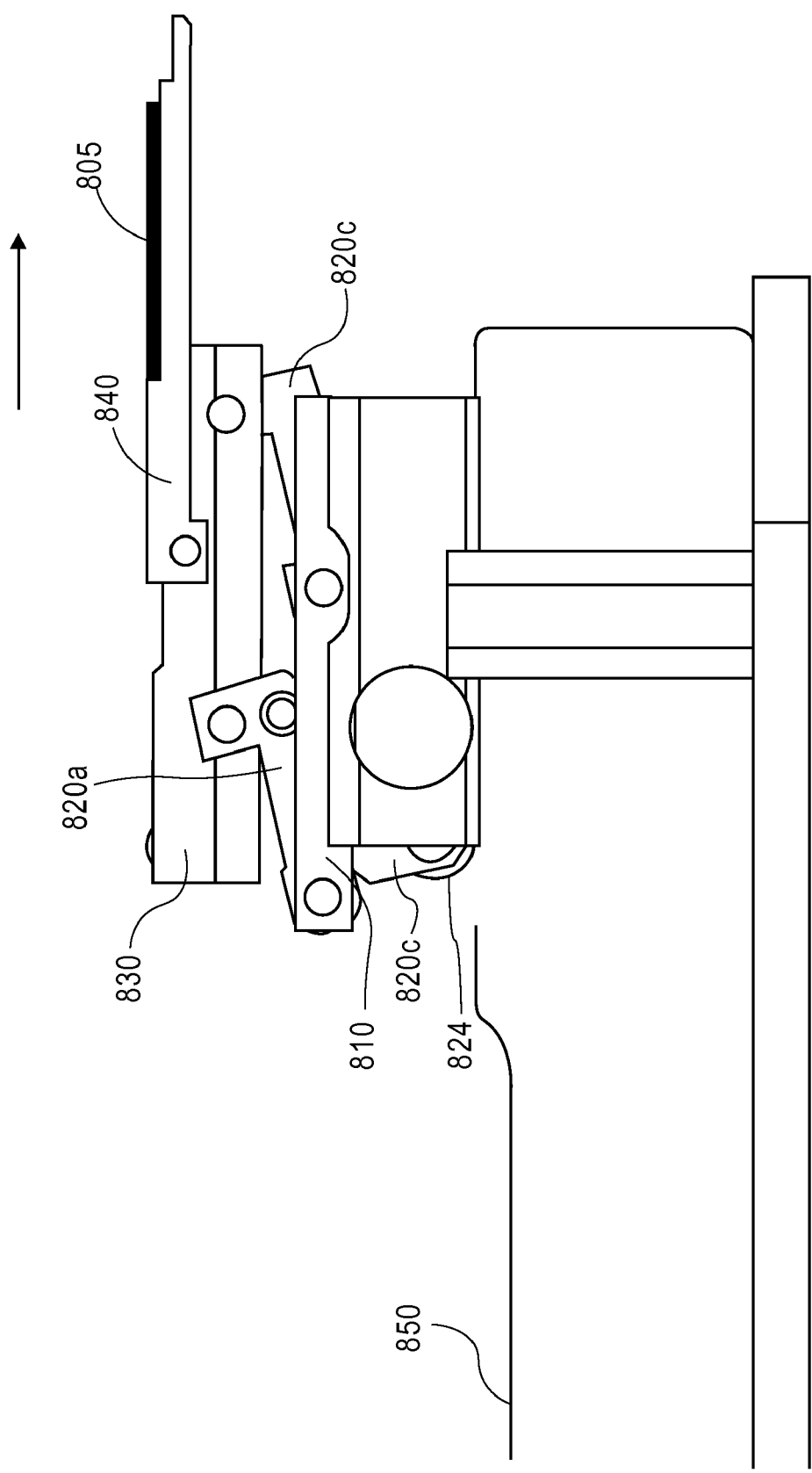
Figure 9I:
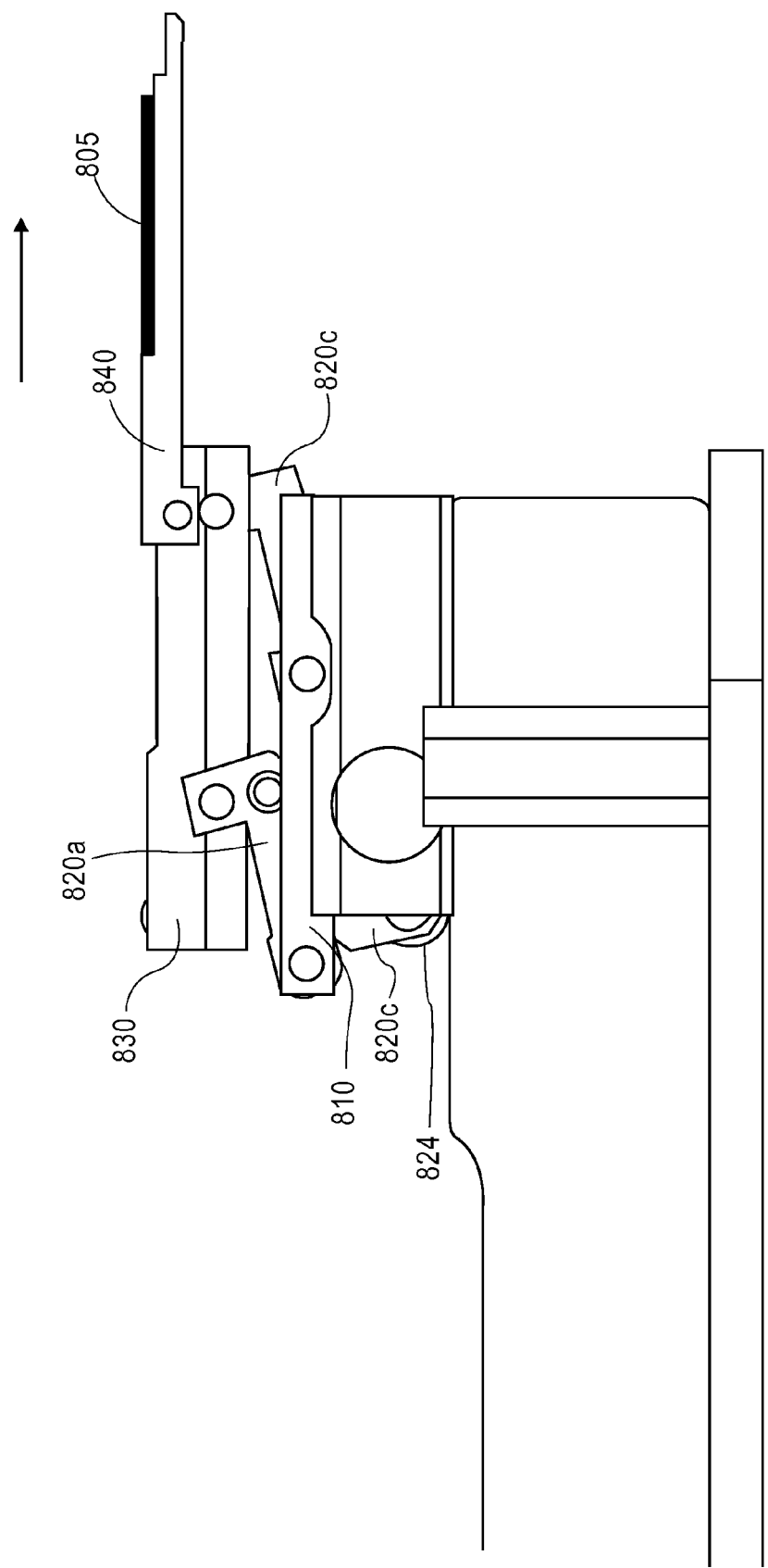

FIGS. 9A-I show how the embodiment shown in FIG. 8 can be used in a slide processing system, such as the ThinPrep® 3000, available from Cytyc Corporation. When the apparatus 800 is used as part of a slide transport system, the apparatus 100 is moved to and from various processing and analysis stations, including a slide cartridge 870. In use, the apparatus 100 moves along the cam 850 to the cartridge 870 to pick a slide 805 from the cartridge and transport the slide 805 to the next station. FIGS. 9B-D illustrate the actuation of the linking members 820a and 820c. FIGS. 9H-I show the fingers 840 being extended outwardly as the apparatus travels along the cam 850. This alternative embodiment provides advantages of increased stability since the slide 805 rests on a separate platform or carrier 830, which is then translated between different elevations. Further, the fingers can be extended outwardly to interface with equipment or processing stations.

The previously described apparatus configurations and method are advantageous compared to conventional slide platforms and slide positioning methods. For example, according to one embodiment, a slide platform that transitions a slide between different elevations while, at the same time, maintaining the slide in a horizontal orientation. Maintaining the slide in a substantially horizontal orientation overcomes a number of shortcomings associated with conventional systems. For example, the slide is more securely transported since the fingers and the slide thereon are not cantilevered between a horizontal orientation and an angled orientation. Further, it is not necessary to push the platform fingers down from an angled orientation, thereby saving positioning processing steps and time. Additionally, mapping software can more easily and accurately determine the location of a slide and slide specimens if the slide is consistently maintained in a substantially horizontal orientation. Moreover, the apparatus can be used for a longer time since the wear and tear on the device is reduced by eliminating repetitive angular adjustments.

Persons skilled in the art will recognize that the above apparatus can be modified in various ways to perform the same horizontal elevation functions. For example, other hinge and linking member arrangements can be utilized. The apparatus can also be adjusted to move the slide to and from different heights or elevations. Further, the design of the linking members can be modified to adapt to other system configurations. Although references have been made in the foregoing description to various embodiments, persons skilled in the art will recognize that insubstantial modifications, alterations, and substitutions can be made to the described embodiments.

What is claimed:

1. An apparatus for carrying a slide within a specimen slide evaluation system, comprising:
    a base;
    a support member for holding the slide;
    a plurality of linking members;
    the plurality of linking members being coupled between the base and the support member, when the plurality of linking members are actuated, the support member remains substantially horizontal when the support member is translated between different elevations.

2. The apparatus of claim 1, the support member comprising a pair of fingers, the slide being placed across the pair of fingers.

3. The apparatus of claim 1, the support member remaining in substantially the same lateral position while being translated between different elevations.

4. The apparatus of claim 1, the support member being moveable between a retracted lateral position and an extended lateral position.

5. The apparatus of claim 1, the plurality of linking members being directly coupled between the base and the support member.

6. The apparatus of claim 1, the plurality of linking members being indirectly coupled between the base and the support member.

7. The apparatus of claim 6, further comprising
    a carrier, the plurality of linking members being coupled between the carrier and the base, the support member being coupled to the carrier.

8. The apparatus of claim 7, wherein when the plurality of linking members are actuated, the carrier and the support member connected thereto remain substantially horizontal when the carrier is translated between different elevations.

9. The apparatus of claim 7, the support member being moveable between a retracted position and an extended position relative to the carrier.

10. The apparatus of claim 7, a majority of the support member extending beyond an outer edge of the carrier in the extended position.

11. The apparatus of claim 7, proximal ends of at least two linking members being connected to the base, distal ends of the at least two linking members being connected to the carrier.

12. The apparatus of claim 7, the plurality of linking members being rotatably coupled to the carrier.

13. The apparatus of claim 6, at least two linking members of the plurality of linking members having an "L" shape.

14. The apparatus of claim 1, the plurality of linking members comprising a linking member on each side of the base.

15. The apparatus of claim 1, wherein two linking members are coupled to opposite sides of the base.

16. The apparatus of claim 15, linking members coupled to opposite sides of the base having substantially the same shape and size.

17. The apparatus of claim 1, at least two linking members moving together in unison.

18. The apparatus of claim 1, at least two linking members moving through about the same angle.

19. The apparatus of claim 1, proximal ends of the plurality of linking members being connected to the base.

20. The apparatus of claim 1, at least two linking members being rotatable in the same plane.

21. The apparatus of claim 1, rotational motion of the plurality of linking members resulting in translation of the slide between different elevations.

22. The apparatus of claim 1, a middle linking member being coupled between the base and proximal ends of two other linking members.

23. The apparatus of claim 22, a distal end of a middle linking member following a cam.

24. The apparatus of claim 1, further comprising
    a carrier, the plurality of linking members being coupled between the carrier and the base, the support member being coupled to the carrier, a middle linking member being coupled between the base and the carrier.

25. The apparatus of claim 24, an end of the middle linking member following a cam.

26. An apparatus for carrying a slide within a specimen slide evaluation system, comprising:
    a base;
    a support member for holding the slide, the support member comprising a pair of fingers, the slide being placed across the pair of fingers;
    a plurality of linking members;
    the plurality of linking members being directly coupled between the base and the support member, when the plurality of linking members are actuated, the support member remains substantially horizontal and in substantially the same lateral position when the support member is translated between different elevations.

27. An apparatus for carrying a slide within a specimen slide evaluation system, comprising:
    a base;
    a support member for holding the slide;
    a plurality of linking members;
    a carrier, the plurality of linking members being coupled between the carrier and the base, the support member being coupled to the carrier so that the plurality of linking members are indirectly coupled between the base and the support member; when the plurality of linking members are actuated, the support member remains substantially horizontal when the support member is translated between different elevations, the support member being moveable between a retracted lateral position and an extended lateral position.

28. The apparatus of claim 27, a majority of the support member extending beyond an outer edge of the carrier when the support member is in an extended position.

29. The apparatus of claim 27, proximal ends of at least two linking members being connected to the base, distal ends of the at least two linking members being connected to the carrier.

30. The apparatus of claim 27, at least two linking members of the plurality of linking members having an "L" shape.

31. The apparatus of claim 27, the support member comprising a pair of fingers. the slide being placed across the pair of fingers.

* * * * *